United States Patent [19]

Kawanishi et al.

[11] Patent Number: 5,598,350
[45] Date of Patent: Jan. 28, 1997

[54] GENETIC MOTIF EXTRACTING METHOD AND APPARATUS

[75] Inventors: Yuichi Kawanishi, Kawasaki; Takashi Gojobori, Mishima; Yoshio Tateno, Mishima; Kazuho Ikeo, Mishima; Masahito Kawai, Kawasaki, all of Japan

[73] Assignees: Fujitsu Limited, Kanagawa; National Institute of Genetics, Shizuoka, both of Japan

[21] Appl. No.: 339,233

[22] Filed: Nov. 10, 1994

[30] Foreign Application Priority Data

Nov. 12, 1993 [JP] Japan ..................................... 5-283329

[51] Int. Cl.⁶ ........................... G06F 19/00; G06F 159/00
[52] U.S. Cl. ......................... 364/496; 382/129; 382/190
[58] Field of Search ............................ 364/496; 382/129, 382/190

[56] References Cited

FOREIGN PATENT DOCUMENTS

0198403A2  10/1986  United Kingdom .

*Primary Examiner*—Edward R. Cosimano
*Attorney, Agent, or Firm*—Armstrong, Westerman, Hattori, McLeland & Naughton

[57] ABSTRACT

A genetic motif extracting apparatus is adapted to extract a motif from genetic sequence information, where the motif has a regularity in a distinctive feature that specifies a genetic function. The genetic motif extracting apparatus includes a weight calculation unit for calculating a weight of each genetic sequence from a length of at least one branch of an evolution tree structure that is related to a plurality of genetic sequences, a score calculation unit for calculating a score that indicates a degree of similarity of sequence elements of the genetic sequences appearing at a site for each site of the genetic sequences using the weight calculated by the weight calculation unit, and a feature information extraction unit for extracting a part of the genetic sequence having the regularity in the distinctive feature as the motif based on the score calculated by the score calculation unit.

9 Claims, 15 Drawing Sheets

F I G. 3

| SEQUENCE A | QVRKSFIHPLYKTKVPRA*VIRPGEDRSHDLMLLHLEEPAKITKAVRVMD |
| SEQUENCE B | LVSKSFPHPGFNMSLLTLKEIPPGADFSNDLMLLRLSKPADITDAVKPIT |
| SEQUENCE C | EVVR*YPKEKF*ICPNKKKNVITDKDIMLIRLDRPVKNSEHIAPLS |
| SEQUENCE D | SAPEPYKR*WYDVQSVVPHPGSRPDSLEDDLILFKLSQNASLGPHVRPLP |
| SEQUENCE E | SAPEPYKR*WYDVQSVVPHPGSRPDSLEDDLILFKLSQNASLGPHVRPLP |

| | | STANDARDIZATION |
|---|---|---|
| SEQUENCE A | 0.615 | 0.210 |
| SEQUENCE B | 0.615 | 0.210 |
| SEQUENCE C | 0.798 | 0.272 |
| SEQUENCE D | 0.452 | 0.154 |
| SEQUENCE E | 0.452 | 0.154 |

FIG. 5

|  | 1 | 2 | 3 | 4 | 5 | 6 | 7 | 8 | 9 | 10 |
|---|---|---|---|---|---|---|---|---|---|---|
| SEQUENCE A: | Q | V | R | K | S | F | I | H | P | L |
| SEQUENCE B: | L | V | S | K | S | F | P | H | P | G |
| SEQUENCE C: | E | V | V | R | * | Y | P | K | E | K |
| SEQUENCE D: | S | A | P | E | P | Y | K | R | * | W |
| SEQUENCE E: | S | A | P | E | P | Y | K | R | * | W |
| G: | — | — | — | — | — | — | — | — | — | 0.2097 |
| A: | — | 0.3083 | — | — | — | — | — | — | — | — |
| S: 0.3083 | — | — | 0.3083 | — | — | — | — | — | — | — |
| T: | — | — | — | — | 0.4194 | — | — | — | — | — |
| P: | — | — | — | — | 0.3083 | — | 0.4820 | — | 0.4194 | — |
| C: | — | — | — | — | — | — | — | — | — | — |
| L: 0.2097 | — | — | — | — | — | — | — | — | — | 0.2097 |
| I: | — | — | — | — | — | — | 0.2097 | — | — | — |
| M: | — | — | — | — | — | — | — | — | — | — |
| V: | — | 0.6917 | 0.2723 | — | — | — | — | — | — | — |
| F: | — | — | — | — | — | 0.4194 | — | — | — | — |
| Y: | — | — | — | — | — | 0.5806 | — | — | — | — |
| W: | — | — | — | — | — | — | — | — | — | 0.3083 |
| D: 0.2723 | — | — | — | 0.3083 | — | — | — | — | 0.2723 | — |
| E: | — | — | — | 0.4194 | — | — | — | — | — | — |
| N: | — | — | — | 0.2723 | — | — | — | — | — | — |
| Q: 0.2097 | — | — | — | — | — | — | — | — | — | — |
| K: | — | — | 0.2097 | — | — | — | 0.3083 | 0.2723 | — | 0.2723 |
| R: | — | — | — | — | — | — | — | 0.3083 | — | — |
| H: | — | — | — | — | — | — | — | 0.4194 | — | — |

FIG. 8

```
                    10        20        30        40        50
             ....+....+....+....+....+....+....+....+....+....+
SEQUENCE A   QVRKSFIHPLYKTKVPRA*VIRPGEDRSHDLNLLHLEEPAKITKAVRVMD
SEQUENCE B   LVSKSFPHPGFNMSLLTLKEIPPGADFSNDLHLLRLSKPADITDAVKPIT
SEQUENCE C   EVVR*YPKEKF***ICPNKKKNVITD**KDIMLIRLDRPVKNSEHIAPLS
SEQUENCE D   SAPEPYKR*WYDVQSVVPHPGSRPDSLEDDLILFKLSQNASLGPHVRPLP
SEQUENCE E   SAPEPYKR*WYDVQSVVPHPGSRPDSLEDDLILFKLSQNASLGPHVRPLP
             ....+....+....+....+....+....+....+....+....+....+

F    F              DLILL L        I  L  ⎫
             Y    Y              IM I           V  I  ⎬ EXTRACTED MOTIF SITES
                                 F                 M  ⎭
```

FIG. 10A

PROBE: FLAA7A-1 (homologue: 53 length: 97) ← ALIGNMENT INFO (PROBE NAME, NUMBER, LENGTH)
Motif extract: window: 1 threshhold: 0.90 ← SET VALUE WHEN EXTRACTING MOTIF SITES
start region size(o): 21 random level(.): 41 ← SET VALUE FOR DETERMINING MOTIF REGION

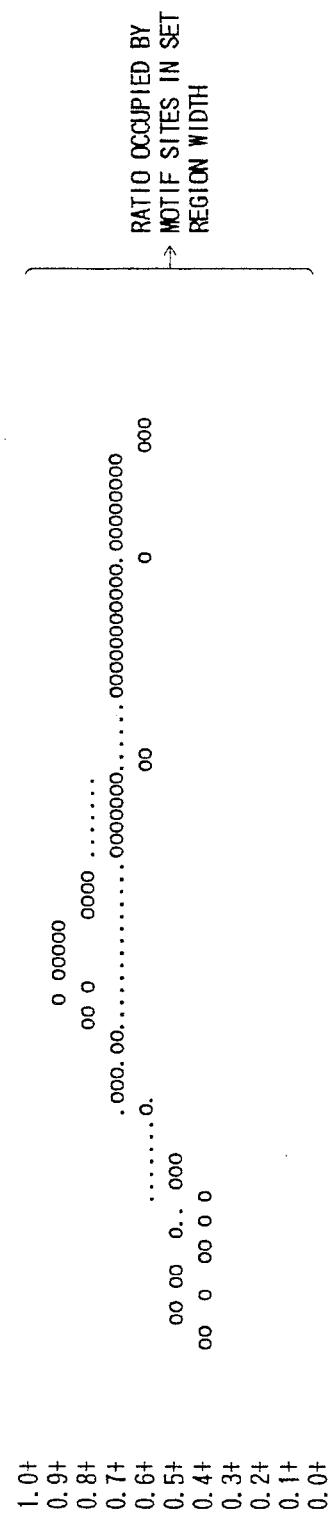

RATIO OCCUPIED BY
MOTIF SITES IN SET
REGION WIDTH

FIG. 10B

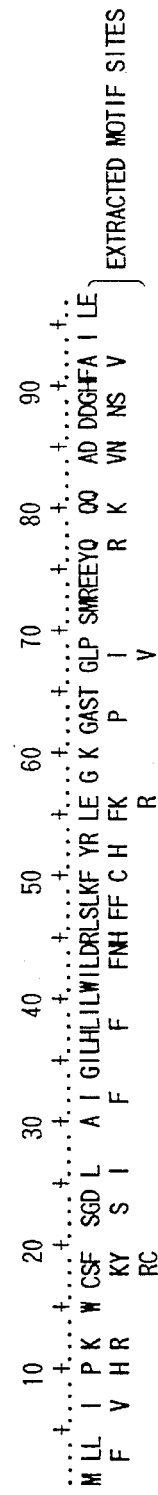

EXTRACTED MOTIF SITES

FIG. 10C

1:M—[LF]L—[IV]—[PH]—[KR]—W—C[SKR][FYC]—S[GS]D—[LI]—A :30
22:S[GS]D—[LI]—A—[IF]—GILH[LF]ILWI[LF][DN] :44
26:[LI]—A—[IF]—GILH[LF]ILWI[LF][DN][RH]JL[SF][LF]K[FC]—[YH]R—[LF][EKR]—G—K :60
55:[LF][EKR]—G—K—G[AP]ST—G[LIV]P—SMREEY[QR]—[QK]Q—[AV][DN] :85
67:G[LIV]P—SMREEY[QR]—[QK]Q—[AV][DN][GS]HF[AV]—I—LE :97

} MOTIF REGIONS

FIG. 11B

```
                    ......                                            oooooooooooooooooooooooooooo
                    oooooo                                          oooooooooooooooooooooooooooooo
         oooooo             o  oooooo                             oooooooooooooooooooooooooooooooo
    o            .....oooo..oooooooooo........                 ooooooooooooooooooooooooooooooooooo
1.0+                     o         o   oo  oo         o  ooo ooo
0.9+      +         +         +         +         +         +         +         +
0.8+     110       120       130       140       150       160       170
0.7+     ...+.........+.........+.........+.........+.........+.........+....
0.6+     EI*MVIGGGRVYEQFLPKAQKLYLTHIDAEVEGDTHFPDYEPDDWESVFSEFHDADAQNSHSYCFQILER****R****
0.5+     EI*MVIGGGRVYEQFLPKAQKLYLTHIDAEVEGDTHFPDYEPDDWESVFSEFHDADAQNSHSYCFQILER****R****
0.4+     EI*MVIGGGRVYEQFLPKAQKLYLTHIDAEVEGDTHFPDYEPDDWESVFSEFHDADAQNSHSYCFEILER****R****
0.3+     EI*MVIGGGRVYDEFLPKAQKLYLTHIDAEVEGDTHFPDYDPDEWESVFSEFHDADAQNSHSYCFEILER****R****
0.2+     EA*MIIGGGQLYAEALPRAQRLYLTYIDAQLNGDTHFPDYLSLGWQELERSTHPADDKNSYACEFVTLSRQ***R****
0.1+     EC*FVIGGAQLYTDLFPYADRLYMTKIHHEFEGDRHFPEFDESNWKLVSSEQGTKDEKNPYDYEFLMYEKKNSSKVGGF
0.0+oo   HV*FIFGGOTLYEAMIDQVDDMYITVIDGKFQGDTFFPPYTFENMEVESSVEGQLDEKNTIPHTFLHLVR****RKGK*
         HV*FIFGGOTLYEAMIDQVDDMYITVIDGKFQGDTFFPPYTFENMEVESSVEGQLDEKNTIPHTFLHLVR****RKGK*
         ETAYVIGGAAIYALFQPHLDRMVLSRVPGEYEGDTYYPEWDAAEWE*L****DAETDHE*GFTLQEWVRSASSR****
         EL*YVAGGAEIYTLALPHAHGVFLSEVHQTFEGDAFFPMLNETEFFELVS*T**E*TIQAVIPYTHSVYAR****RNG**
         QELVIAGGAQIFTAFKDDVDTLLVTRLAGSFEGDTKMIPLNWDDFTKVSSRTVE*DTNPALTHTYEV**W*QKKA
         HV*IVSGGGEIYRETLPMASTLHISTIDIEPEGDVFFPNIPNT*FEVVF*E**Q*HFSSNINYCYQIW*QKG
         .....+.........+.........+.........+.........+.........+.........+....
         110       120       130       140       150       160       170

GG     LF     LL    EGD
                IY     MI     N    M
                V      VM     Q    F
                       V           Y

ECODHFOLG-1
ECOFOLX-1
ECOFOLA-1
KPNFOLA-1
PAZDHFRA-1
BACTHYDA-2
STATN4003-3
STADHFR-1
HALDHFRV-1
ECODHFRA-1
LBADHFR-1
LMODHFRV-2
```

FIG. 11C

```
 13: A------IG----[LIM]PW-----[DE]---[IFY][KR] :39
 49: [LMV][GA]R-T-[EN]S[IMF]----LP :63
 62: LP-----[IV] :69
107: GG--[LIV][FY]---------[LMV] :122
122: [LMV]-[LIMV]-------[ENQ]GD--[MFY] :137
```

FIG. 12B

```
                    1.0+
                    0.9+
                    0.8+
                    0.7+
                    0.6+
                    0.5+
                    0.4+
                    0.3+
                    0.2+
                    0.1+ooooo
                    0.0+
                                110
                        ....+....+
    HUMTRX1-1       LEATI*NELV
    HUMTHD-1        LEATI*NELV
    RATTR-1         LEATI*TEFA
    CHKTHD-1        LEETI*KSLV
    YSCTRIA-1       IKQAI*ASNV
    YSCTRX2-1       IKQAI*ASNV
    YSCTRX1-1       IKQAI*AANA
    YSCTRILA-1      IKQAI*AANA
    ANITRXM-1       LANTLDKHL*
    ANATRXA-1       LSQTLEKHL*
    STYTRXA-1       LKEFLDANLA
    ECOTRXA-1       LKEFLDANLA
    ECOTRX-1        LKEFLDANLA
    ECORHOA-1       LKEFLDANLA
    RCATRXA-1       LATWIASAL*
    BACAPKII-1      LQELVNKHL*
                                110
                        ....+....+
                        L   L
                        I   I
                            V
```

FIG. 12C

```
13: [FY] :13
25: [IV]--DF-A-WCGPC[KR]-[IV]-P----[LIF] :47
61: [DN]-D-----[AP] :69
69: [AP]-------[TIM]P[AT][LF]--[LFY]K-G-------G------[LI]---[LIV] :105
```

GENETIC MOTIF EXTRACTING METHOD AND APPARATUS

BACKGROUND OF THE INVENTION

The present invention generally relates to genetic motif extracting methods and apparatuses, and more particularly to a genetic motif extracting method for extracting a motif that is a conserved region or site among a plurality of genetic sequences by comparing a plurality of genetic sequence information, and to an apparatus which employs such a genetic motif extracting method.

Due to the recent progress made in genetic engineering, there are increased number of genetic sequence information databases representing DNA sequences or amino acid sequences. In addition, attempts to elucidate all genetic sequences of specific organisms are being made on a world wide basis, such as the human genome project, and it is expected that the genetic sequence information will rapidly increase in the future.

Among such genetic sequences, there are many genetic sequences whose sequence information is known but the functions and structures thereof are unknown. As an effective method of predicting the functions and structures of the genes from the sequence information, there is the method of retrieving motifs, that is, regularities in the distinctive features of the genetic sequences. Therefore, there is a need to realize a technique for extracting a large number of motifs from the genetic sequences whose sequences are known.

Conventionally, the motifs which specify the genetic functions in the genetic sequences and indicate the regularities of the distinctive features of the sequences have been determined based on experiments and reports in literature. A database called PROSITE is known as a database which registers such motifs.

It is known that, in general, the functionally important regions or sites of the genetic sequences are less likely to change. By utilizing this fact, it is possible to extract the motifs as conserved regions or sites of the genetic sequences, through comparison of the genetic sequences. However, a technique for extracting the motifs through comparison of a plurality of genetic sequences has not been established.

It would require considerably work to determine the motifs by human work based on experiments or the like. Hence, it may be regarded that a large amount of information effective for the purposes of elucidating the genetic functions can be obtained if it is possible to extract the motifs mechanically, that is, automatically, from a comparison of the genetic sequences. However, the following problems occur if the sites of the genetic sequences are simply compared and the similarities of the sites are checked.

In other words, if the plurality of genetic sequence information which is the subject of the motif extraction is biased to specific organisms, the regularities or distinctive features that are to be extracted become biased. For example, suppose that a large amount of genetic sequence information related to advanced organisms such as genetic sequence information of humans, genetic sequence information of monkeys and genetic sequence information of horses exists, and the motifs are to be extracted from sequence information groups having a small amount of genetic sequence information related to less advanced organisms based on the similarities of the sites. In such a case, it cannot necessarily be concluded that the sites with high similarities are the conserved sites which did not change much during the evolution process. On the other hand, it cannot necessarily be concluded that the sites with low similarities are not conserved sites. Therefore, there is a possibility that the conserved sites which are extracted as the motifs may be erroneously concluded,

SUMMARY OF THE INVENTION

Accordingly, it is a general object of the present invention to provide a novel and useful genetic motif extracting method and apparatus in which the problems described above are eliminated.

Another and more specific object of the present invention is to provide a genetic motif extracting apparatus adapted to extract a motif from genetic sequence information, where the motif has a regularity in a distinctive feature that specifies a genetic function, and the genetic motif extracting apparatus comprises weight calculation means for calculating a weight of each genetic sequence from a length of at least one branch of an evolution tree structure that is related to a plurality of genetic sequences, score calculation means for calculating a score that indicates a degree of similarity of sequence elements of the genetic sequences appearing at a site for each site of the genetic sequences using the weight calculated by the weight calculation means, and feature information extraction means for extracting a part of the genetic sequence having the regularity in the distinctive feature as the motif based on the score calculated by the score calculation means. According to the genetic motif extracting apparatus of the present invention, it is possible to extract and identify the motif region at a high speed because it is possible to mechanically, that is, automatically, extract and identify the motif region from the genetic sequence information. Hence, it is possible to easily find a new motif from an extremely large amount of genetic sequence data and to make a motif database with ease. Based on the motif information obtained by the present invention, it is possible to efficiently predict the functions and structures of the genetic sequences having unknown functions. As a result, the present invention is extremely useful when applied to the finding of genetic functions and identification of functional regions, and the present invention can greatly contribute to the development of genetic engineering.

Still another object of the present invention is to provide a genetic motif extracting method for extracting a motif from genetic sequence information, where the motif has a regularity in a distinctive feature that specifies a genetic function, and the genetic motif extracting method comprises the steps of (a) inputting alignment data of a plurality of genetic sequences subject to extraction of the motif, (b) generating an evolution tree structure based on the alignment data input in the step (a), (c) calculating a weight of each genetic sequence from a length of at least one branch of the evolution tree structure, (d) calculating a score that indicates a degree of similarity of sequence elements of the genetic sequences appearing at a site for each site of the genetic sequences using the weight calculated by the weight calculation means and similarity information related to the sequence elements obtained in advance depending on types of the sequence elements, and (e) extracting a site as a motif site when the score calculated at the site exceeds a predetermined or set threshold value. According to the genetic motif extracting method of the present invention, it is possible to extract and identify the motif region at a high speed because it is possible to mechanically, that is, automatically, extract and identify the motif region from the genetic sequence information. Hence, it is possible to easily find a new motif from an extremely large amount of genetic sequence data and to make a motif database with ease. Based on the motif information obtained by the present invention, it is possible to efficiently predict the functions and structures of the genetic sequences having unknown functions. As a result, the present invention is extremely useful when applied to the finding of genetic functions and identification of functional regions, and the present invention can greatly contribute to the development of genetic engineering.

Other objects and further features of the present invention will be apparent from the following detailed description when read in conjunction with the accompanying drawings.

BRIEF DESCRIPTION OF THE DRAWINGS

FIG. 3 is a diagram showing input alignment data;

FIG. 5 is a diagram showing the calculated weights of amino acids at each site;

FIG. 8 is a diagram showing a motif site extracted in the embodiment of the genetic motif extracting apparatus;

FIGS. 10A, 10B and 10C respectively are diagrams showing results of an experiment obtained when a motif region identification process is carried out;

FIGS. 11A, 11B and 11C respectively are diagrams showing results of an experiment obtained when a motif region identification process is carried out; and FIGS. 12A, 12B and 12C respectively are diagrams showing results of an experiment obtained when a motif region identification process is carried out.

DESCRIPTION OF THE PREFERRED EMBODIMENTS

Figure 1:
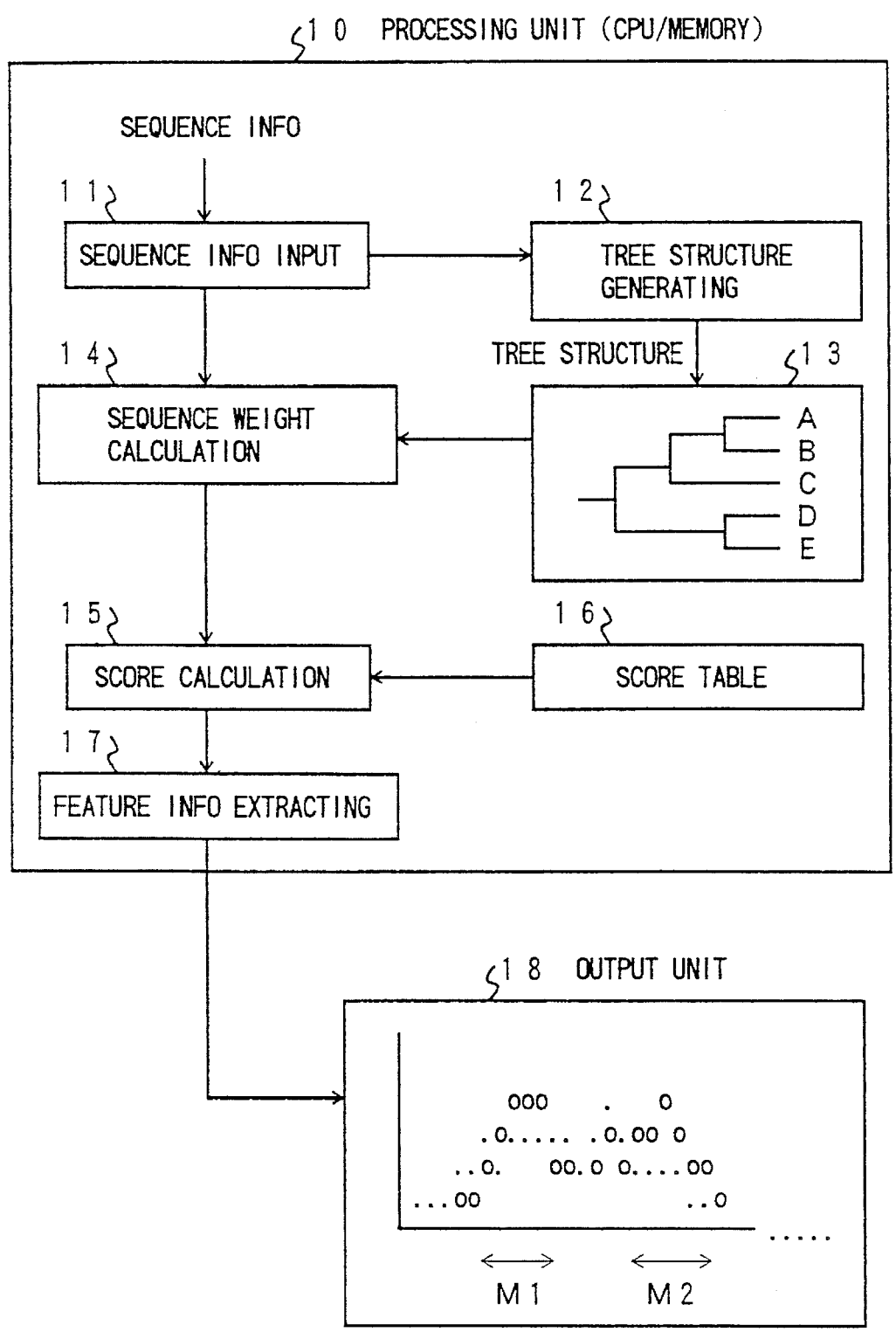
FIG. 1 is a system block diagram showing an embodiment of a genetic motif extracting apparatus according to the present invention.

FIG. 1 shows an embodiment of a genetic motif extracting apparatus according to the present invention.

The genetic motif extracting apparatus shown in FIG. 1 generally includes a processing unit 10 and an output unit 18. The processing unit 10 has a known construction including a central processing unit (CPU), and a memory for storing programs to be executed by the CPU and data. Of course, a plurality of memories may be connected to the CPU, such as a read only memory (ROM) for storing the programs and a random access memory (RAM) for storing data.

The CPU and the memory or memories of the processing unit 10 together form a sequence information input means 11, a tree structure generating means 12, an evolution tree structure 13, a sequence weight calculation means 14, a score calculation means 15, a score table 16, and a feature information extraction means 17.

The sequence information input means 11 inputs alignment data related to a plurality of genetic sequences which are the subject of the motif extraction. The tree structure generating means 12 generates the tree structure 13 from the alignment data related to the plurality of genetic sequence input by the sequence information input means 11, based on variations of the genetic sequences. For example, the tree structure 13 may be generated in advance using paleontological information or the like.

The sequence weight calculation means 14 calculates the weight of each genetic sequence from the lengths of the branches of the tree structure 13. The scope calculation means 15 calculates the score that is indicative of the degree of similarity of the sequence elements appearing at each of the sites of the genetic sequences, based on the weights of the genetic sequences and the score table 16. The score table 16 is based on the similarity of elements obtained in advance depending on the types of sequence elements.

The feature information extraction means 17 extracts, as a motif site, the site having a regularity of the distinctive feature in the genetic sequences, based on the calculated score. In addition, the feature information extraction means 17 calculates the frequency of appearance (or appearance rate) of the motif sites within a predetermined width of a continuous region or within a set width of a continuous region. If the calculated appearance rate exceeds a predetermined random level or a set random level, the continuous region is regarded as a motif region, and mutually adjacent motif regions are regarded as one motif region. Such calculation results of the feature information extraction means 17 are supplied to the output unit 18.

The output unit 18 is a display, a printer or the like. The output unit 18 makes an output in a graph form, for example, by plotting the appearance rate of the motif sites, the random level and the like.

In this embodiment of the genetic motif extracting apparatus, the sequence information input means 11 inputs multiple alignment data. The output unit 18 outputs the amino acids having a high degree of conservation within the genetic sequences which form the alignment data as the motifs at each site. In FIG. 1, an example of the display made by the output unit 18 shows extracted motifs M1 and M2, a plot of the random level indicated by " . . . ", and a plot of the appearance rate of the motif sites within the continuous region indicated by "o".

The tree structure 13 is generated based on the alignment data in order to correct the frequency of appearance of the amino acids from becoming biased due to the existence of evolutionally related genetic sequences, and the weighting with respect to each genetic sequence is made depending on the lengths of branches and shapes of the branches in the tree structure 13. In addition, in order to permit the appearance of amino acids having similar characteristics, the score at each site is calculated using the score table 16 which is calculated based on the similarities of the amino acids. The higher the calculated score is at a certain site, the higher the degree of conservation of the amino acids is at the certain site.

Furthermore, an operation of setting a threshold value TH of the score is carried out in order to extract the motif site. Moreover, the site where a score exceeding this set threshold value TH is indicated is extracted as the motif site.

In addition, in order to limit the motif region, an operation is carried out to set the width of the region and the random level. If the appearance rate of the motif sites within the set width of the region indicates a value exceeding the random level, this region is regarded as the motif region. Further, the mutually adjacent motif regions are regarded as one motif region.

Figure 2:
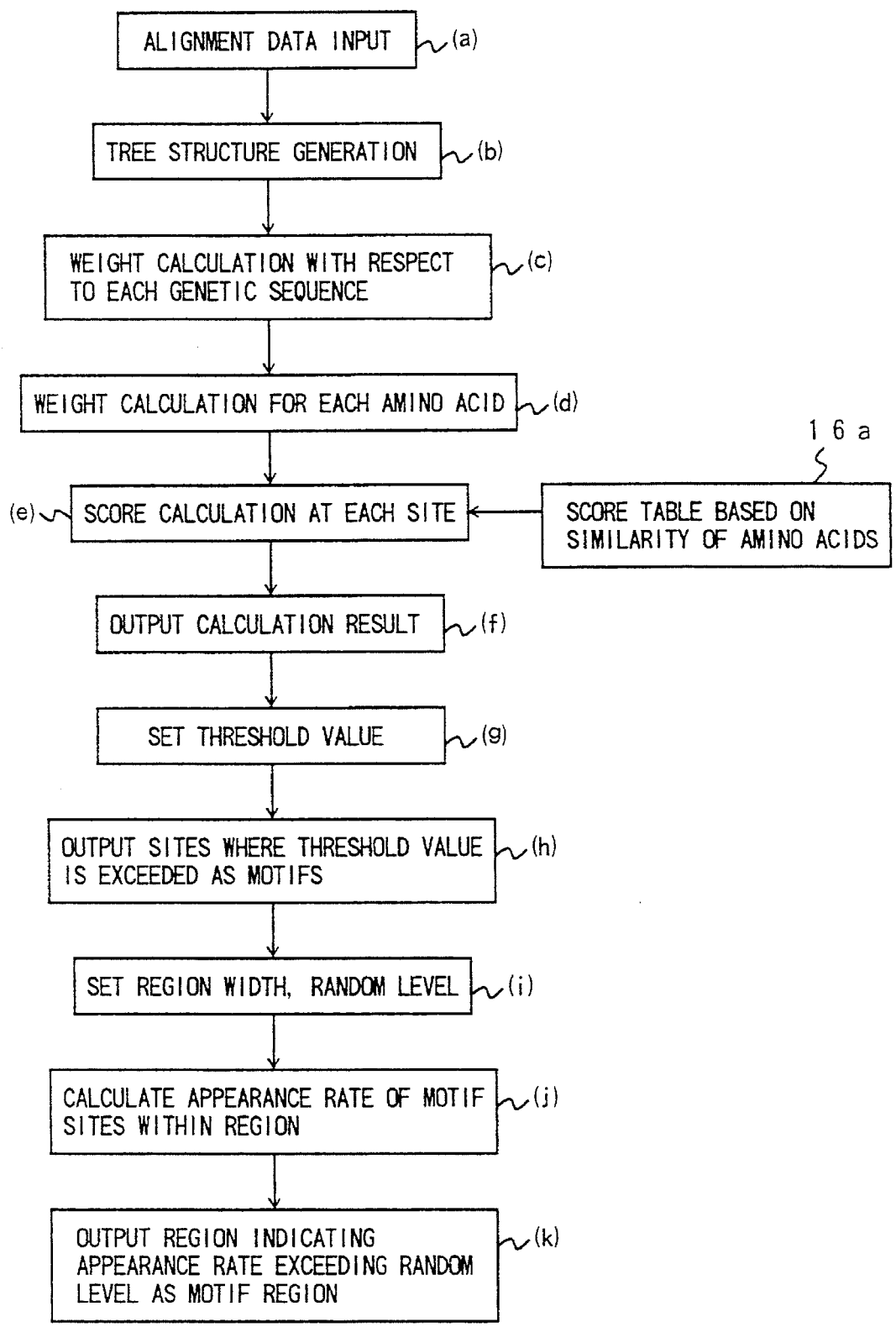
FIG. 2 is a flow chart showing an embodiment of a genetic motif extracting method according to the present invention.

Next, a description will be given of an embodiment of a genetic motif extracting method according to the present invention, by referring to FIG. 2. The process shown in FIG. 2 is carried out by the processing unit 10 shown in FIG. 1. In this embodiment, it is assumed for the sake of convenience that the genetic sequence information is represented by amino acid sequences.

In the following description, (a) through (k) correspond to steps (a) through (k) shown in FIG. 2.

(a) Alignment Data Input:

The sequence information input means 11 inputs alignment data of five genetic sequences A through E shown in FIG. 3 in a step (a) shown in FIG. 2. In FIG. 3, one letter of the alphabet corresponds to one amino acid, and a symbol "*" within the genetic sequences A through E represents a gap.

When the amino acids representing each of the sites are obtained from their frequency of appearance, the obtained amino acids will become biased. For this reason, in the following process, the tree structure 13 is generated from the input alignment data, and the weight calculation with respect to each of the genetic sequences is made based on the lengths and shapes of the branches in the tree structure 13. The bias correction is made by weighting each genetic sequence using the calculated weight.

(b) Tree Structure Generation:

The tree structure generating means 12 generates the tree structure 13 in a step (b) shown in FIG. 2, using the unweighted pair-group clustering (UPG) technique, for example. However, it is of course possible to use other techniques to generate the tree structure 13. Particularly, in this embodiment of the genetic motif extracting method, the tree structure 13 is generated in the following manner.

First, variations of the genetic sequences are obtained based on the alignment data. The variation is obtained by forming a pair of genetic sequences and calculating the variation as substitution numbers of the amino acids between the two genetic sequences. The following formula (1) which is generally used when obtaining the amino acid substitution number is used in this embodiment, where K denotes the amino acid substitution number and p denotes a ratio of the sites having different amino acids between the two genetic sequences. The site including the gap is excluded from this calculation.

$$K = -log(1-p) \quad (1)$$

The variation is calculated for all pairs of genetic sequences, that is, for all of the pairs (A, B), (A, C), ..., (A, E), (B, C), ..., (C, D), (C, E), (D, E). When the calculated variations for these pairs of genetic sequences are denoted by VAB, VAC, ..., VDE, the pair having the smallest variation is selected from the variations VAB, VAC, ..., VDE and the genetic sequences forming this pair are related. In this particular case, the genetic sequences D and E are related, and the variance VDE of this pair is set as the length of the branch.

Next, the genetic sequences D and E are regarded as one group, and the variation of this group with respect to each of the other genetic sequences are similarly calculated based on the formula (1). For example, the variation $V_{(DE)A}$ between the pair of genetic sequences D and E and the genetic sequence A can be obtained from $V_{(DE)A}=(V_{AD}+V_{AE})/2$. Similarly, the variations $V_{(DE)B}$ and $V_{(DE)C}$ are calculated, and a minimum variation is selected from such calculated variations and the previously obtained variations $V_{AB}$, $V_{AC}$, ... excluding the variation $V_{DE}$. In this particular case, the variation VAB between the genetic sequences A and B is the minimum, and these genetic sequences A and B form a second group. Thereafter, the grouping of the genetic sequences and the calculation of the variations are carried out in a manner to the above, and the tree structure 13 is generated based on the results of such grouping of the genetic sequences and the calculation of the variations.

Figures 4A, 4B:
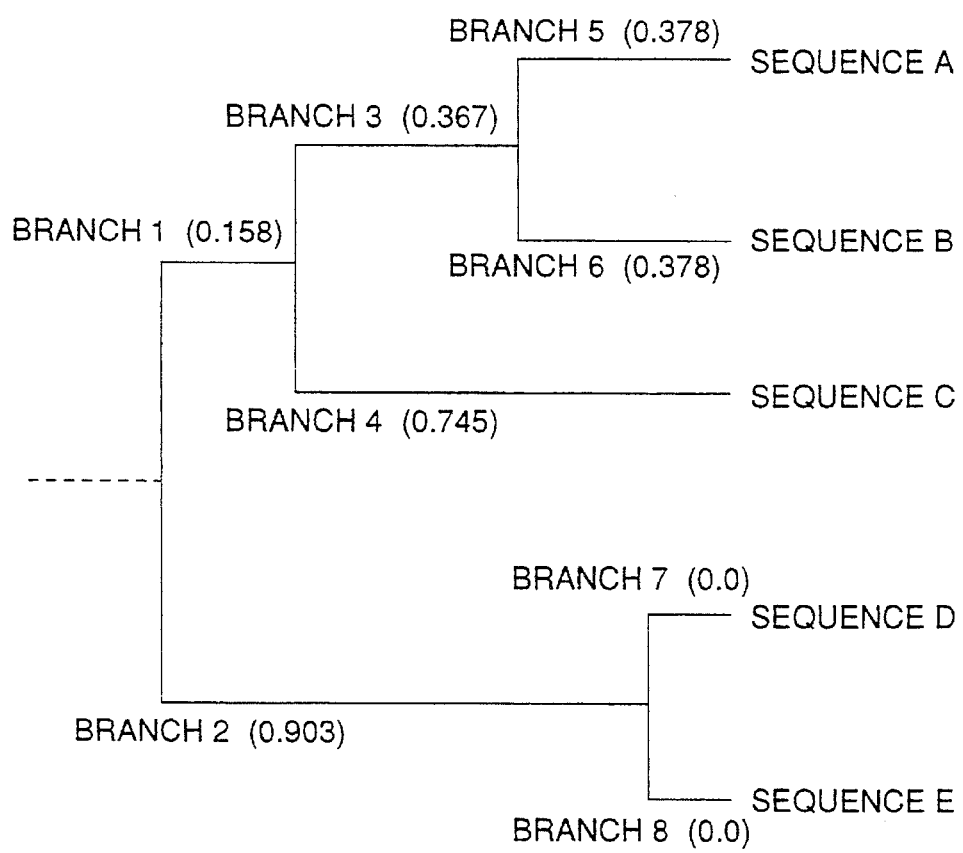
FIG. 4A is a diagram showing a tree structure obtained from the alignment data shown in FIG. 3.
FIG. 4B is a diagram showing the weight of each genetic sequence obtained from the alignment data shown in FIG. 3.

FIG. 4A shows the tree structure 13 that is generated based on the alignment data shown in FIG. 3. In FIG. 4A, the numerals in brackets represent the lengths of the branches in the tree structure 13.

(c) Weight Calculation With Respect to Each Genetic Sequence:

The sequence weight calculation means 14 carries out a weighting process with respect to each branch of the tree structure 13 in a step (c) shown in FIG. 2, based on the lengths of each of the branches in the generated tree structure 13. The weight to be given to each branch is obtained by dividing the length of the branch by the number of genetic sequences branching from this branch.

In the tree structure 13 shown in FIG. 4A, a branch 1 has a length 0.158, and three genetic sequences A, B and C branch from this branch 1. Accordingly, the weight of this branch 1 can be obtained from 0.158/3=0.053. The weights of all of the other remaining branches 2 through 7 can be obtained similarly as follows.

Weight of branch 1=0.158/3=0.053

Weight of branch 2=0.903/2=0.452

Weight of branch 3=0.387/2=0.184

Weight of branch 4=0.745

Weight of branch 5=Weight of branch 6=0.378/2=0.189

Weight of branch 7=Weight of branch 8=0.000

The weight of each genetic sequence is calculated based on the weights of each of the branches obtained in the above described manner.

More particularly, the weight to be given to each genetic sequence is obtained as a sum total of the weights of the branches that are passed when the branches of the tree structure 13 are traced upstream from the root.

In the case of the tree structure shown in FIG. 4A, the branches 1, 3 and 5 are passed when the tree structure 13 is traced upstream from the root. In this case, the weights given to these branches 1, 3 and 5 respectively are 0.053, 0.184 and 0.378. Accordingly, the weight of the genetic sequence A can be obtained from 0.053+0.184+0.378=0.615. Similarly, the weights with respect to all of the genetic sequences A through E are calculated. Furthermore, a sum total of the weights of all of the genetic sequences A through E is obtained, and the weights of each of the genetic sequences A through E are respectively divided by the sum total and standardized to obtain standardized weights, so that a sum total of the standardized weights becomes 1. FIG. 4B shows the weights and the standardized weights of each of the genetic sequences A through E which are obtained from the tree structure 13 shown in FIG. 4A.

(d) Weight Calculation For Each Amino Acid:

Next, the sequence weight calculation means 14 obtains the weights of the amino acids at each of the sites in a step (d) in FIG. 2, based on the standardized weights of the genetic sequences A through E. The weight of an amino acid that appears at each site is obtained as a sum total of the weights of all of the genetic sequences in which this amino acid appears.

A description will be given of the process carried out by the sequence weight calculation means 14 based on the alignment data shown in FIG. 3 and the weights of the genetic sequences A through E shown in FIG. 4B. At a first site, Q (glutamine) appears in the genetic sequence A, L (leucine) appears in the genetic sequence B, E (glutamine acid) appears in the genetic sequence C, and S (serine) appears in the genetic sequences D and E as the amino acids, respectively. Accordingly, at the first site, the standardized weight 0.210 of the genetic sequence is given to the amino acid Q, the standardized weight 0.210 is given to the amino acid L, the standardized weight 0.272 is given to the amino acid E, and a weight 0.308 which is a sum of the standardized weights of the genetic sequences D and E is given to the amino acid S. The weight 0 is given to the other amino acids at this first site.

Similarly, at a second site, an amino acid V (valine) appears in the genetic sequences A, B and C, and an amino acid A (alanine) appears in the genetic sequences D and E. The weight of the amino acid V at this second site is given by a sum of the standardized weights of the genetic sequences A, B and C, that is, 0.210+0.210+0.272=0.692. The weight of the amino acid A at this second site is given by 0.154+0.154=0.308.

The weight of each amino acid is calculated for all of the sites in a manner similar to the above. FIG. 5 shows the weights of the amino acids at the first through tenth sites calculated in the above described manner. FIG. 5 only shows the calculation results down to the fourth places of the decimal.

Figure 6:
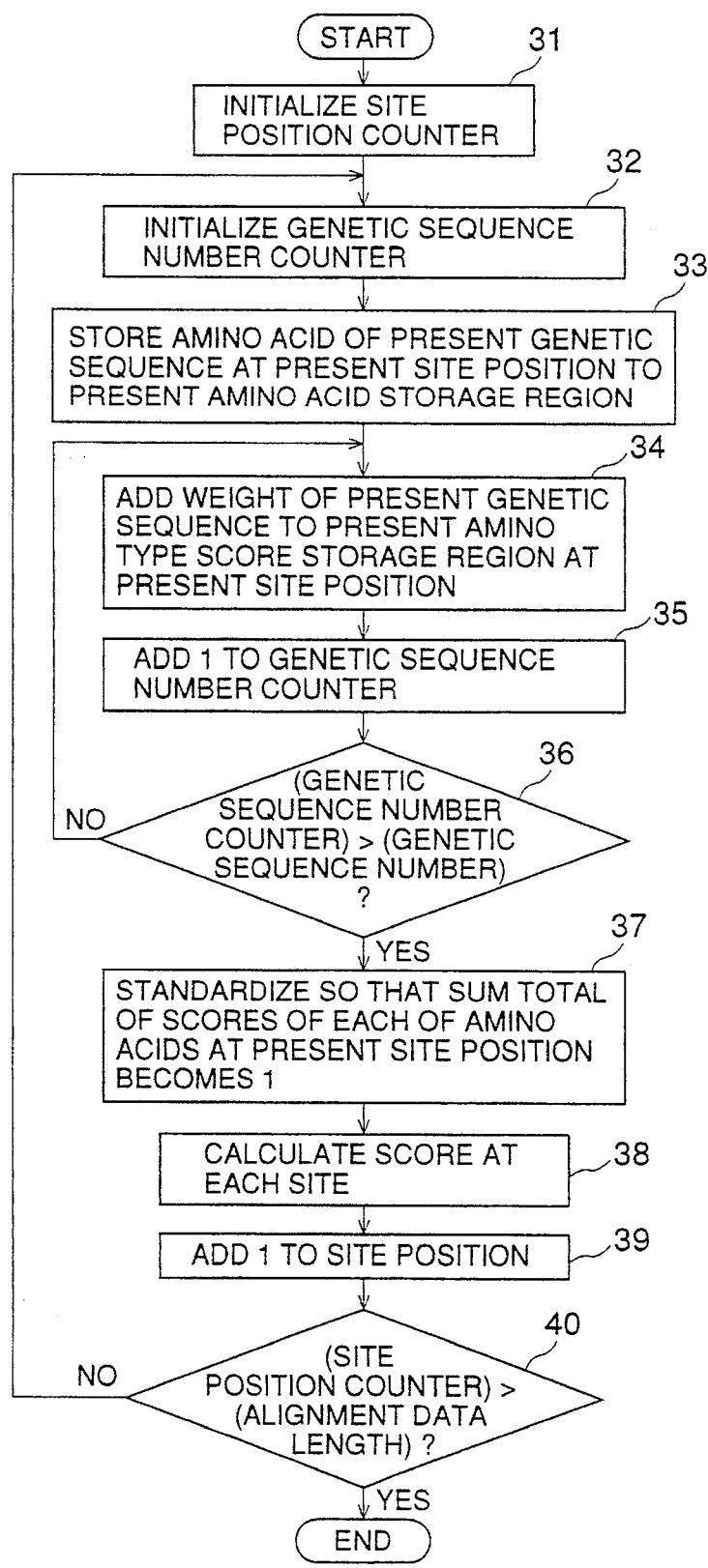
FIG. 6 is a flow chart showing an embodiment of a process carried out by a sequence weight calculation means shown in FIG. 1.

FIG. 6 is a flow chart showing an embodiment of the process that is carried out by the sequence weight calculation means 14 in the step (d) shown in FIG. 2.

In FIG. 6, a step 31 initializes a site position counter within the sequence weight calculation means 14, that is, within the CPU of the processing unit 10. A step 32 initializes a genetic sequence number counter within the sequence weight calculation means 14, that is, within the CPU of the processing unit 10. A step 33 stores the amino acid of a present genetic sequence at a present site position into a present amino acid type storage region within the sequence weight calculation means 14, that is, within the memory of the processing unit 10. In the following description., the present site position, the present genetic sequence, the present amino acid type and the like respectively indicate the position of the site to which the attention is presently made, the genetic sequence to which the attention is presently made, the amino acid type to which the attention is presently made and the like. A step 34 adds the weight of the present genetic sequence the score that is stored in a score storage region of the present amino acid type for the present site position, within the sequence weight calculation means 14, that is, within the memory of the processing unit 10, and stores the added value in the score storage region. A step 35 adds 1 to a genetic sequence number counter.

A step 36 decides whether or not the value of the genetic sequence number counter is greater than the number of genetic sequences, and the process returns to the step 34 if the decision result in the step 36 is NO. On the other hand, if the decision result in the step 36 is YES, a step 37 carries out a standardizing process so that a sum total of the scores of each of the amino acids at the present site position becomes 1. Next, a step 38 calculates the score at each site, and a step 39 adds 1 to the site position. A step 40 decides whether or not the value of the site position counter is greater than the length of the alignment data, and the process ends if the decision result in the step 40 is YES. On the other hand, if the decision result in the step 40 is NO, the process returns to the step 32.

(e) Score Calculation At Each Site:

Depending on the genetic sequence, there are cases where a substitution to an amino acid having a similar characteristic occurs. However, even in such cases, the functions are in many cases conserved even after the substitution. Accordingly, in order to extract such sites as the motifs, the score calculation means 15 calculates the score at each site from the store table that is based on the similarities of the physical chemistry among the amino acids.

A score table 16a that is based on the similarities of the amino acids is obtained in advance from the physical chemistry characteristics of each of the amino acids. The score table 16a has a value given with respect to each pair of amino acids based on a distance that indicates the extent of the differences between the substitution frequencies and characteristics of the amino acids forming the pair. For example, the following values are given as the scores of the pairs of amino acids having glycine (G) as one of the amino acids forming each pair, where each score is multiplied by 100 for the sake of convenience.

Glycine (G) & Glycine 100.0

Glycine (G) & Alanine 74.0

Glycine (G) & Serine (S) 75.7

Glycine (G) & Leucine (L) 0.0

Various kinds of score tables including that described above are known, and a description of the various kinds of score tables will be omitted in this specification.

The score at each site calculated using the values in the score table 16a indicates that the amino acid is conservative at the site when the value of the score is large. For example, the score at the first site in FIG. 5 can be obtained from the following formula (2), where $S_1$ represents the score at the first site, D(amino acid 1, amino acid 2) represents the similarity of the amino acid 1 and the amino acid 2 obtained from the score table 16a, and S(amino acid) represents the weight of the amino acid at the site shown in FIG. 5.

$$S_1 = D(S, S) \cdot S(S) \cdot S(S) + D(S, L) \cdot S(S) \cdot S(L) + \quad (2)$$

$$D(S, E) \cdot S(S) \cdot S(E) + D(S, Q) \cdot S(S) \cdot S(Q) +$$

$$D(L, S) \cdot S(L) \cdot S(S) + D(L, L) \cdot S(L) \cdot S(L) +$$

$$D(L, E) \cdot S(L) \cdot S(E) + D(L, Q) \cdot S(L) \cdot S(Q) +$$

$$D(E, S) \cdot S(E) \cdot S(S) + D(E, L) \cdot S(E) \cdot S(L) +$$

$$D(E, E) \cdot S(E) \cdot S(E) + D(E, Q) \cdot S(E) \cdot S(Q) +$$

$$D(Q, S) \cdot S(Q) \cdot S(S) + D(Q, L) \cdot S(Q) \cdot S(L) +$$

$$D(Q, E) \cdot S(Q) \cdot S(E) + D(Q, Q) \cdot S(S) \cdot S(Q)$$

Figure 7:
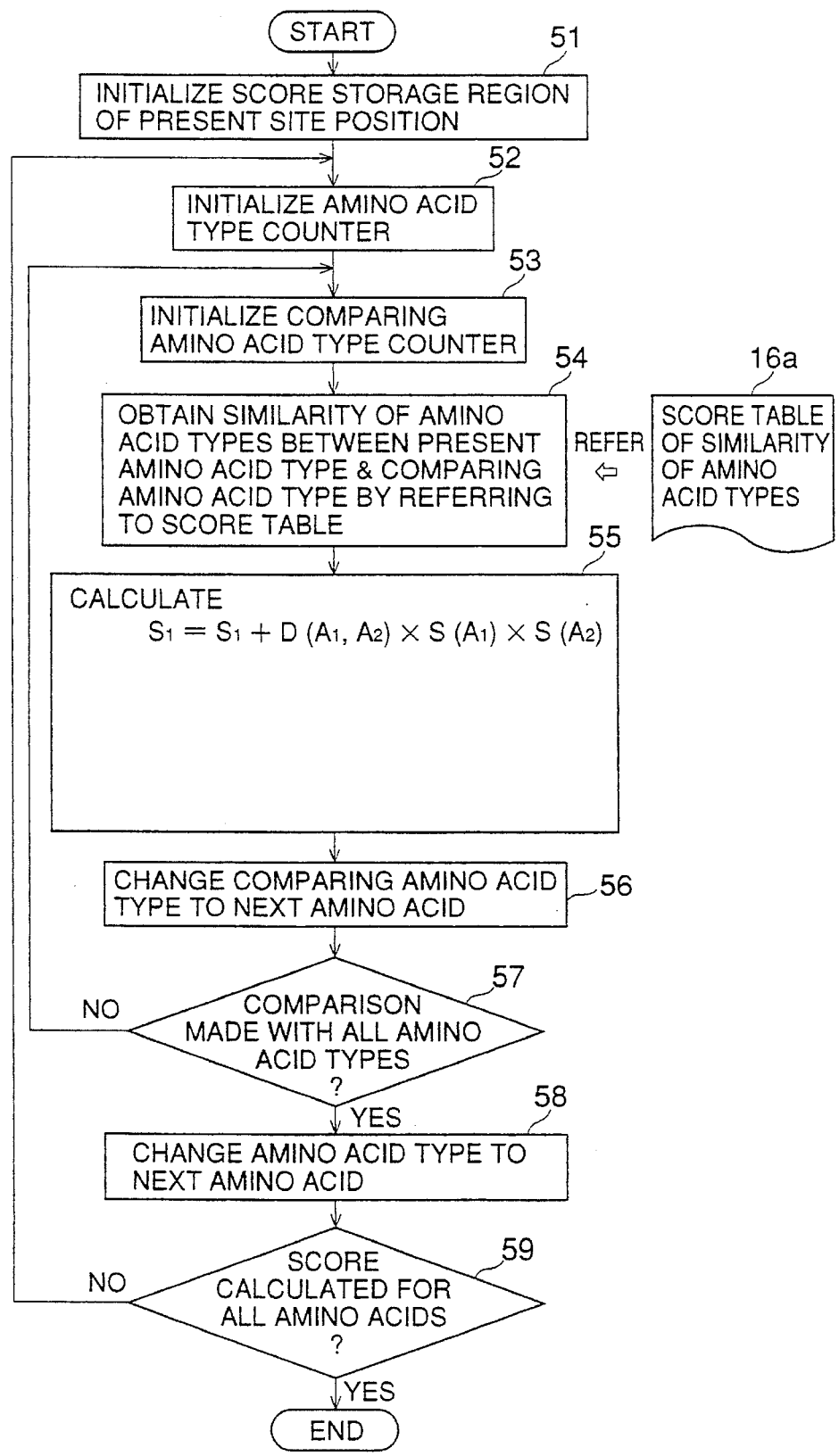
FIG. 7 is a flow chart showing an embodiment of a process carried out by a score weight calculation means shown in FIG. 1.

FIG. 7 is a flow chart showing an embodiment of the process carried out by the step (e) shown in FIG. 2.

In FIG. 7, a step 51 initializes a score storage region for the present site position in the score calculation means 15, that is, within the memory of the processing unit 10. A step 52 initializes an amino acid type counter in the score calculation means 15, that is, within the memory of the processing unit 10. A step 53 initializes a comparing amino acid type counter in the score calculation means 15, within the memory of the processing unit 10. A step 54 obtains the similarity between the present amino acid type and the present comparing amino acid type by making a reference to the amino acid similarity score table 16a.

A step 55 carries out a calculation described by $S_i=S_i+D(A_1, A_2)\cdot S(A_1)\cdot S(A_2)$, where $S_i$ represents the score at the present site position (ith site), $A_1$ represents the present amino acid type, $A_2$ represents the present comparing amino acid type, $D(A_1, A_2)$ represents the score of the similarity between the present amino acid type and the present comparing amino acid type, $S(A_1)$ represents the score of the present amino acid type at the present site position, and $S(A_2)$ represents the score of the present comparing amino acid type at the present site position.

A step 56 changes the comparing amino acid type to a next comparing amino acid type, and a step 57 decides whether or not the comparison has been made for all amino acid types. The process returns to the step 53 if the decision result in the step 57 is NO. On the other hand, if the decision result in the step 57 is YES, a step 58 changes the amino acid type to a next amino acid type. A step 59 decides whether or not the calculation of the score has been made for all amino acid types, and the process ends if the decision result in the step 59 is YES. On the other hand, the process returns to the step 52 if the decision result in the step 59 is NO.

(f) Output of Calculation Result:

The calculation results of the scores calculated in the score calculation means 15 for the alignment data shown in FIG. 3 are as follows.

| Sites 01 to 05 | 0.5183 | 0.7744 | 0.5677 | 0.8198 | 0.4881 |
| --- | --- | --- | --- | --- | --- |
| Sites 06 to 10 | 0.9328 | 0.4940 | 0.8683 | 0.3165 | 0.3580 |
| Sites 11 to 15 | 0.9311 | 0.3834 | 0.4072 | 0.3611 | 0.6114 |
| Sites 16 to 20 | 0.6937 | 0.5976 | 0.5699 | 0.5574 | 0.5010 |
| Sites 21 to 25 | 0.3880 | 0.6168 | 0.5530 | 0.5739 | 0.6296 |
| Sites 26 to 30 | 0.7718 | 0.3473 | 0.3772 | 0.6956 | 1.0000 |
| Sites 31 to 35 | 0.9841 | 0.9646 | 1.0000 | 0.9149 | 0.8891 |
| Sites 36 to 40 | 1.0000 | 0.6916 | 0.7864 | 0.7804 | 0.7903 |
| Sites 41 to 45 | 0.5830 | 0.6021 | 0.7753 | 0.5654 | 0.6976 |
| Sites 46 to 50 | 0.9037 | 0.6428 | 0.8303 | 0.9542 | 0.7105 |

(g) Setting Threshold Value:

The feature information extraction means 17 determines a threshold value for the score, and extracts the site that is given a score exceeding the threshold value as the motif. The threshold value is specified by the user or is determined in advance as a default value.

(h) Outputting Sites Where Threshold Value Is Exceeded As Motifs:

When the threshold value of the score is represented by TH, the feature information extraction means 17 extracts the sites which satisfy the following relationship as the candidates of the motifs.

$$S>TH$$

The following motif is extracted from the alignment data shown in FIG. 3 when the threshold value TH of the score is TH=0.90.

30 *D* [*LI*] [*IM*] *L* [*LIF*] [*KRH*] *L*

In the extracted motif above, "30" indicates that the position of the leading amino acid of the motif within the alignment data shown in FIG. 3 is 30. In addition, the element within the brackets "[ ]" indicates that the plurality of amino acids within the brackets appear at the site. In other words, the extracted motis are the 6th site (F or Y), the 11th site (F or Y), the 30th site (D), the 31st site (L or I), the 32nd site (I or M), the 33rd site (L), the 34th site (L or I or F), the 36th site (L), the 46th site (I or V) and the 49th site (L or I or M).

FIG. 8 is a diagram showing the motif sites extracted in this embodiment.

Conventionally, it was possible to extract the site having the distinctive sequence pattern in the genetic sequence as the motif by a manual operation to a certain extent, however, it was difficult to identify a region as the motif. But when identifying the functional regions and presuming ancestor genes, it is very important that the region is identified as the motif. Hence, a more detailed description will now be given of a method of identifying the region as the sequence of motifs that are extracted as sites in the present invention.

Figure 9:
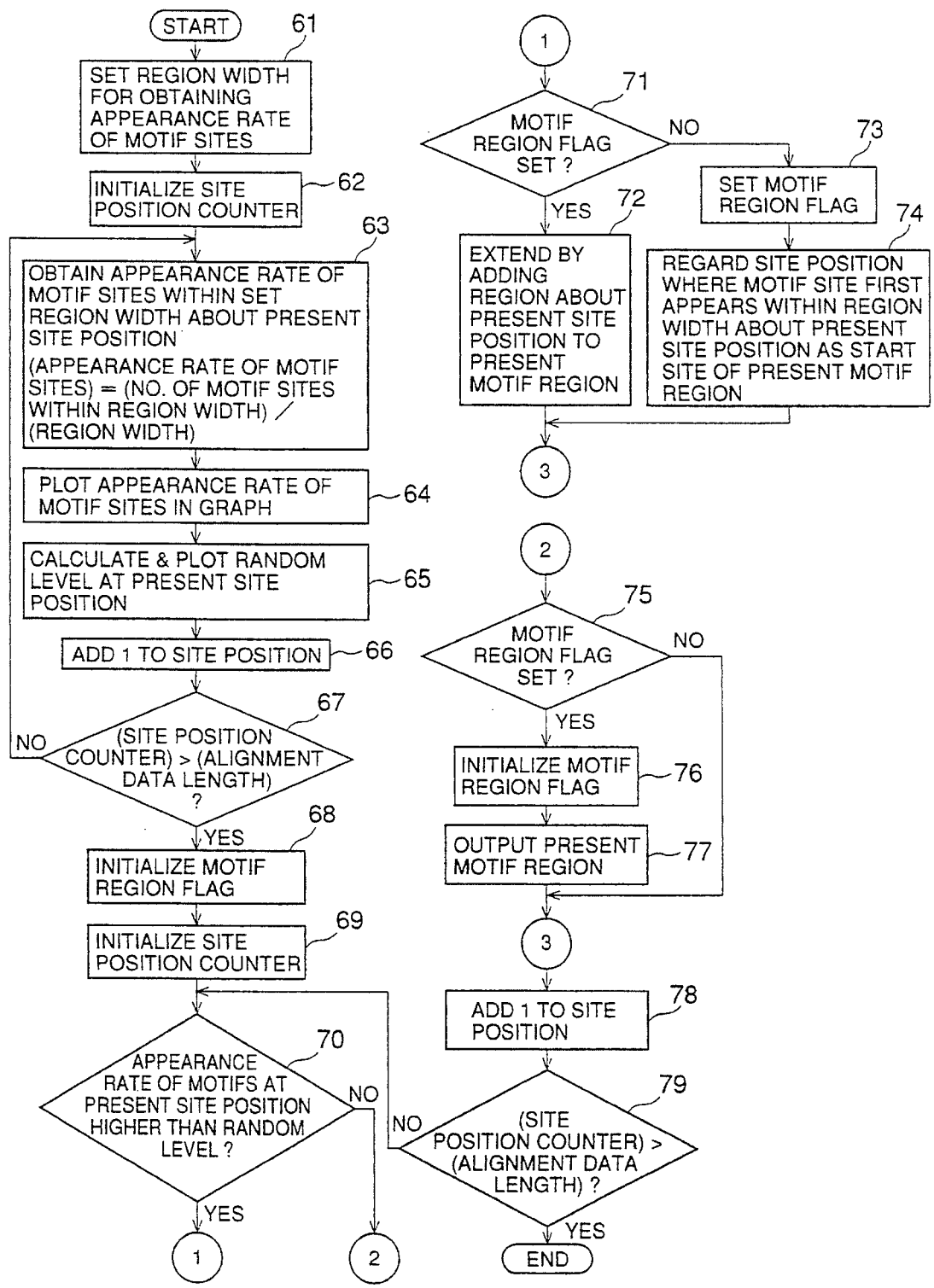
FIG. 9 is a flow chart showing an embodiment of a process carried out by a feature information extraction means shown in FIG. 1.

(i), (j) & (k) Setting Region Width, Calculating Appearance Rate of Motif Sites & Outputting Motif Region:

FIG. 9 is a flow chart showing an embodiment of the processes carried out by the feature information extraction means 17 in the steps (i), (j) and (k) shown in FIG. 2.

In this embodiment, there basically are three processes. In a first process, an arbitrary region width is set, and an appearance rate of motif sites within this set region width is obtained. In a second process, a random level is obtained for the purpose of deciding whether or not the appearance rate of the motif sites within the set region width is sufficiently high, and if the motif sites exist at the appearance rate exceeding the random level, the motif sites within this region width are identified as one motif region. In a third step, if the identified motif regions are continuous, these motif regions as a whole are regarded as one motif region.

More particularly, the following steps S1 through S6 are repeated.

A step S1 extracts the motif sites.

A step S2 sets an initial region width, an extension width, and a maximum extension width. In addition, this step S2 sets the region width for obtaining the random level of the appearance rate of the motif sites to the maximum extension width. In this case, if the maximum extension width exceeds one-half the length of the alignment data, the region width of the random level is set to a value not exceeding one-half the length of the alignment data.

A step S3 calculates the appearance rate of the motif sites for each of the initial region width and the region width of the random level, and plots the calculated appearance rates.

A step S4 regards the initial region width as a "motif region" when the appearance rate of the motif sites in the initial region width exceeds the appearance rate of the motif sites in the region width of the random level.

When the appearance rates of the motif sites in the two mutually adjacent initial region widths are both "motif regions", a step S5 integrates the two motif regions into one "motif region".

A step S6 repeats the steps S4 and S5 for the entire length of the alignment data.

The process of identifying the motif region will now be described with reference to FIG. 9. In FIG. 9, a step 61 sets the region width for obtaining the appearance rate of the motif sites. A step 62 initializes a site position counter of the feature information extraction means 17, that is, within the CPU of the processing unit 10. A step 63 regards the present site position as the center, and obtains the appearance rate of the motif sites within the set region width from the following formula.

(Appearance rate of motif sites)=(Number of motif sites within region width)/(Region width)

A step 64 plots the appearance rate of the motif sites on a graph. A step 65 calculates the random level at the present site position, and plots the random level on the graph. A step 66 adds "1" to the site position, and a step 67 decides whether or not the value of the site position counter is greater than the length of the alignment data. The process returns to the step 63 if the decision result in the step 67 is NO.

On the other hand, if the decision result in the step 67 is YES, a step 68 initializes a motif region flag of the feature information extraction means 17, that is, within the CPU of the processing unit 10. A step 69 initializes the site position counter. A step 70 decides whether or not the appearance rate of the motif at the site position is higher than the random level. The process advances to a step 71 if the decision result in the step 70 is YES, and the process advances to a step 75 if the decision result in the step 70 is NO.

The step 71 decides whether or not the motif region flag is set. If the decision result in the step 71 is YES, a step 72 adds the region having the present site position as its center to the present motif region and extends the present motif region. On the other hand, if the decision result in the step 71 is NO, a step 73 sets the motif region flag, and a step 74 regards the site position where the motif site appears first within the region width having the present site position as its center as the start site of the present motif region. After the step 72 or 74, the process advances to a step 78.

The step 75 decides whether or not the motif region flag is set. The process advances to the step 78 if the decision result in the step 75 is NO. On the other hand, if the decision result in the step 75 is YES, a step 76 initializes the motif region flag, and a step 77 outputs the present motif region. After this step 76, the process advances to the step 78.

The step 78 adds "1" to the site position. In addition, a step 79 decides whether or not the value of the site position counter is greater than the length of the alignment data. The process ends if the decision result in the step 79 is YES. On the other hand, if the decision result in the step 79 is NO, the process returns to the step 70.

A description will now be given of the results of the experiments that were obtained when the above described process of identifying the motif region was carried out.

In the experiment, the identification of the motif region was made with respect to the alignment data using FLAA7A-1 as the probe. FIGS. 10A, 10B and 10C show the results which were obtained for a case where the probe name is FLAA7A-1, the homologue number is 53, the initial region width is 21, the maximum extension width is 101, the length of the alignment data is 97, the region width for obtaining the random level is 41, and the set value at the time of extracting the motif site is 0.90.

FIG. 10A shows the ratio of the set region width occupied by the motif sites, where "o" indicates the plot for the initial value of the motif region width, and "..." indicates the plot of the random level. In FIG. 10A, the plot having the higher ratio is plotted and shown with a priority over the other at parts where the plots overlap.

FIG. 10B shows the extracted motif sites.

Furthermore, FIG. 10C shows the motif regions that are obtained by the process of identifying the motif region In FIG. 10C, ":" indicates the start position and the end position of the motif, "[ ]" indicates that a plurality of amino acids appear at the motif site, and "-" indicates that an arbitrary amino acid or a gap appears at the site. The site indicated by "-" corresponds to a site that is not a motif site.

Figure 11A:
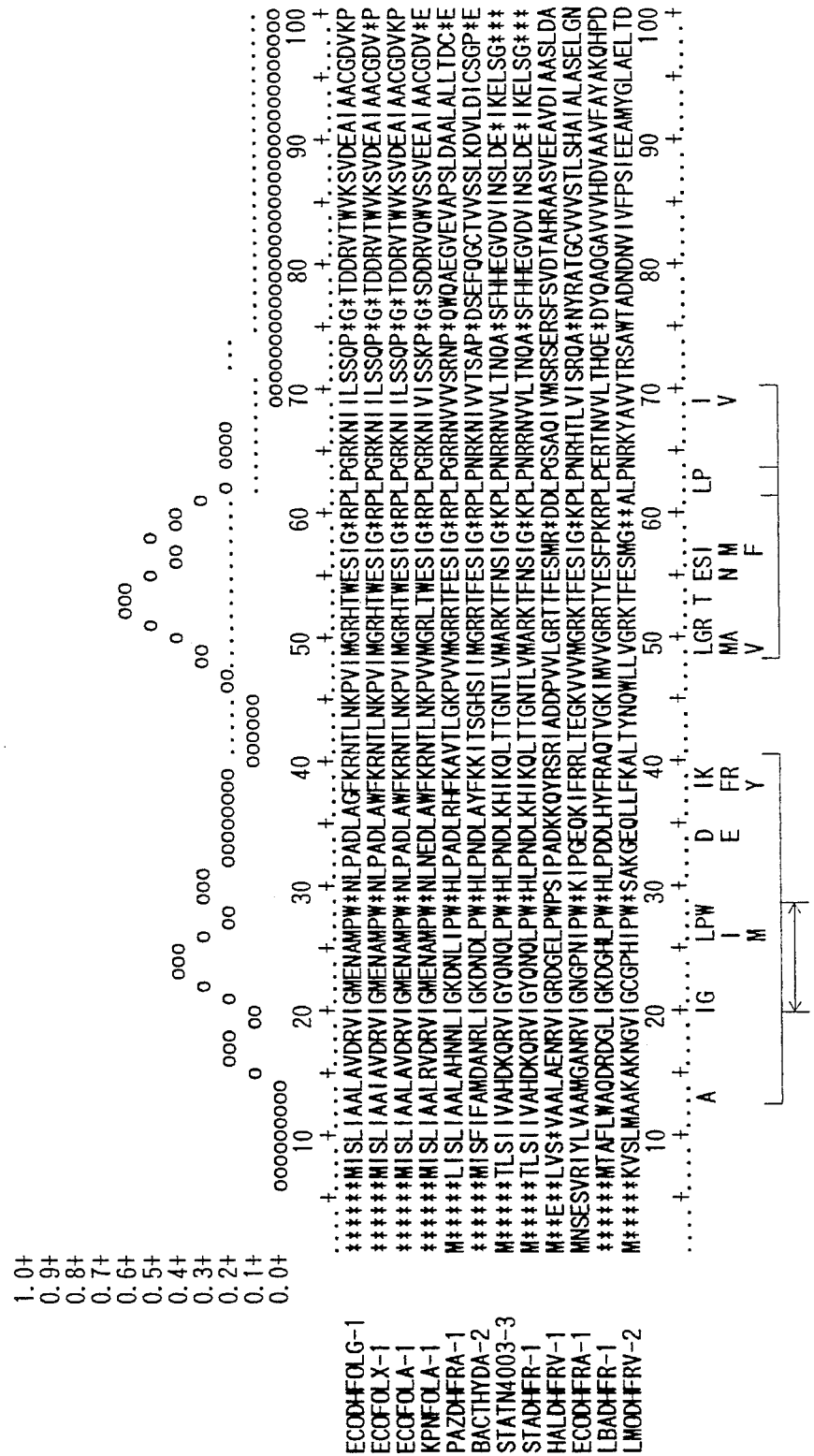

FIGS. 11A, 11B and 11C show the results of another experiment made with respect to the alignment data using ECODHFOLG-1 as the probe. The results shown in FIGS. 11A, 11B and 11C were obtained for a case where the probe name is ECODHFOLG-1, the homologue number is 11, the initial region width is 11, the length of the alignment data is 179, the region width for obtaining the random level is 81, and the set value at the time of extracting the motif site is 0.90. FIGS. 11A and 11B show the plots with respect to the same alignment data in two divisions for the sake of convenience. On the other hand, FIG. 11C shows the motif regions that are obtained by the process of identifying the motif region.

FIGS. 11A and 11B show the ratio of the set region width occupied by the motif sites in correspondence with the alignment data, where "o" indicates the plot for the initial value of the motif region width, that is, the appearance rate of the motif sites in the set region width, and "..." indicates the plot of the random level. If the appearance rate of the motif sites is lower than the random level, these motif sites are not regarded as a motif region. In FIGS. 11A and 11B, the plot having the higher ratio is plotted and shown with a priority over the other at parts where the plots overlap. In addition, in FIGS. 11A and 11B, the names shown on the left side of the alignment data indicate the entry names of the genetic sequences registered in a genetic sequence database DDBJ. Furthermore, Dihydrofolate reductase signature [LIF]-G-X(4)-[LIVMF]-P-W is a data registered in the motif database PROSITE.

In FIG. 11C, the numerals such as "122" shown on the left side indicate the start position of each motif region in the alignment data. In addition, the numerals such as "137" shown on the right side indicate the end position of each motif region in the alignment data.

Figure 12A:
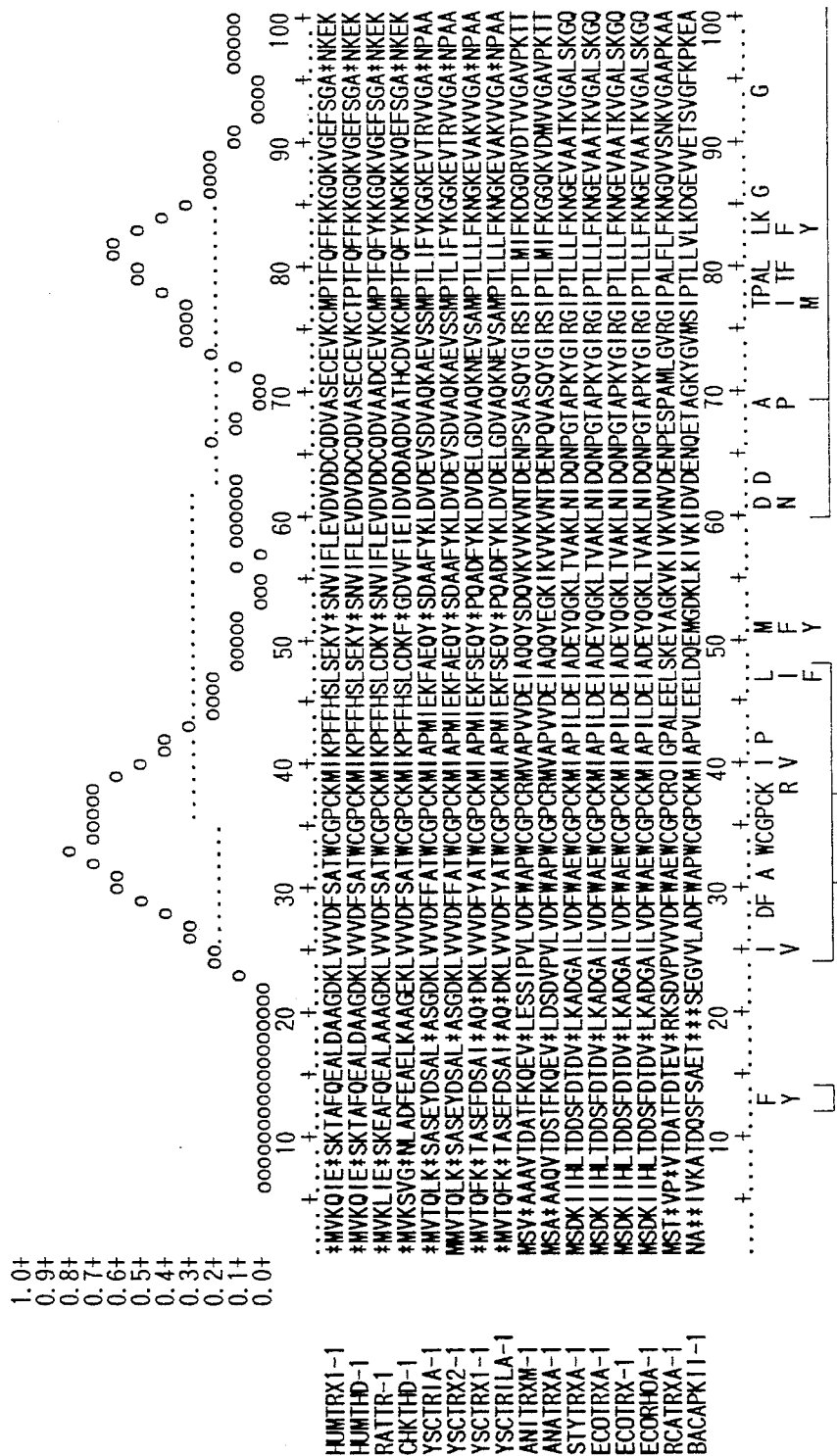

FIGS. 12A, 12B and 12C show the results of still another experiment made with respect to the alignment data using HUMTRXI-1 as the probe. The results shown in FIGS. 12A, 12B and 12C were obtained for a case where the probe name is HUMTRX1-1, the homologue number is 15, the initial region width is 11, the length of the alignment data is 110, the region width for obtaining the random level is 51, and the set value at the time of extracting the motif site is 0.90. FIGS. 12A and 12B show the plots with respect to the same alignment data in two divisions for the sake of convenience. On the other hand, FIG. 12C shows the motif regions that are obtained by the process of identifying the motif region.

FIGS. 12A and 12B show the ratio of the set region width occupied by the motif sites in correspondence with the alignment data, where "o" indicates the plot for the initial value of the motif region width, that is, the appearance rate of the motif sites in the set region width, and "..." indicates the plot of the random level. If the appearance rate of the motif sites is lower than the random level, these motif sites are not regarded as a motif region. In FIGS. 12A and 12B, the plot having the higher ratio is plotted and shown with a priority over the other at parts where the plots overlap. In addition, in FIGS. 12A and 12B, the names shown on the left side of the alignment data indicate the entry names of the genetic sequences registered in the genetic sequence database DDBJ. Furthermore, Thioredoxin family active site [STA]-X-[WG]-C-[AGV]-[PH]-C is a data registered in the motif database PROSITE.

In FIG. 12C, the numerals such as "69" shown on the left side indicate the start position of each motif region in the alignment data. In addition, the numerals such as "105" shown on the right side indicate the end position of each motif region in the alignment data.

Therefore, according to the present invention, it is possible to extract and identify the motif region at a high speed because it is possible to mechanically, that is, automatically, extract and identify the motif region from the genetic sequence information. Hence, it is possible to easily find a new motif from an extremely large amount of genetic sequence data and to make a motif database with ease. Based on the motif information obtained by the present invention, it is possible to efficiently predict the functions and structures of the genetic sequences having unknown functions. As a result, the present invention is extremely useful when applied to the finding of genetic functions and identification of functional regions.

Further, the present invention is not limited to these embodiments, but various variations and modifications may be made without departing from the scope of the present invention.

What is claimed is:

1. A genetic motif extracting apparatus adapted to extract a motif from genetic sequence information, said motif having a regularity in a distinctive feature that specifies a genetic function, said genetic motif extracting apparatus comprising:

weight calculation means for calculating a weight of each genetic sequence from a length of at least one branch of an evolution tree structure that is related to a plurality of genetic sequences;

score calculation means for calculating a score that indicates a degree of similarity of sequence elements of the genetic sequences appearing at a site for each site of the genetic sequences using the weight calculated by said weight calculation means; and feature information extraction means for extracting a part of the genetic sequence having the regularity in the distinctive feature as the motif based on the score calculated by said score calculation means.

2. The genetic motif extracting apparatus as claimed in claim 1, which further comprises:

tree structure generating means for generating the evolution tree structure related to differences among the genetic sequences based on alignment data of the plurality of genetic sequences.

3. The genetic motif extracting apparatus as claimed in claim 1, wherein said score calculation means includes means for calculating the score based on the weight of each genetic sequence calculated by said weight calculation means and similarity information of sequence elements that are obtained in advance depending on types of the sequence elements.

4. The genetic motif extracting apparatus as claimed in claim 1, wherein said feature information extraction means includes means for extracting a site as a motif site when the score for the site calculated by said score calculation means exceeds a predetermined or set threshold value.

5. The genetic motif extracting apparatus as claimed in claim 4, wherein said feature information extraction means further includes means for calculating an appearance rate of motif sites within a predetermined or set width of a continuous region to extract the continuous region as a motif region when the appearance rate exceeds a predetermined or set random level, and for integrating mutually adjacent motif regions as one motif region to output the one motif region.

6. The genetic motif extracting apparatus as claimed in claim 5, which further comprises:

output means for outputting feature information obtained from said feature information extraction means in a graph form display so that at least the appearance rate of the motif sites and values of the random level are plotted in the graph form display.

7. A genetic motif extracting method for extracting a motif from genetic sequence information, said motif having a regularity in a distinctive feature that specifies a genetic function, said genetic motif extracting method comprising the steps of:

(a) inputting alignment data of a plurality of genetic sequences subject to extraction of the motif;

(b) generating an evolution tree structure based on the alignment data input in said step (a);

(c) calculating a weight of each genetic sequence from a length of at least one branch of the evolution tree structure;

(d) calculating a score that indicates a degree of similarity of sequence elements of the genetic sequences appearing at a site for each site of the genetic sequences using the weight calculated by said weight calculation means and similarity information related to the sequence elements obtained in advance depending on types of the sequence elements; and (e) extracting a site as a motif site if the score calculated for the site exceeds a predetermined or set threshold value.

8. The genetic motif extracting method as claimed in claim 7, which further comprises the steps of:

(f) calculating an appearance rate of motif sites within a predetermined or set width of a continuous region to extract the continuous region as a motif region when the appearance rate exceeds a predetermined or set random level, and for integrating mutually adjacent motif regions as one motif region to output the one motif region.

9. The genetic motif extracting method as claimed in claim 8, which further comprises the steps of:

(g) outputting feature information obtained by said steps (e) and (f) in a graph form display so that at least the appearance rate of the motif sites and values of the random level are plotted in the graph form display.

* * * * *